United States Patent
Weber et al.

(10) Patent No.: US 12,102,482 B2
(45) Date of Patent: Oct. 1, 2024

(54) METHODS AND SYSTEMS FOR ADJUSTING THE FIELD OF VIEW OF AN ULTRASOUND PROBE

(71) Applicant: KONINKLIJKE PHILIPS N.V., Eindhoven (NL)

(72) Inventors: Frank Michael Weber, Hamburg (DE); Irina Waechter-Stehle, Hamburg (DE); Tobias Wissel, Lubeck (DE); Arne Ewald, Hamburg (DE); Matthias Lenga, Mainz (DE); Jochen Peters, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 425 days.

(21) Appl. No.: 17/438,964

(22) PCT Filed: Mar. 13, 2020

(86) PCT No.: PCT/EP2020/056913
§ 371 (c)(1),
(2) Date: Sep. 14, 2021

(87) PCT Pub. No.: WO2020/187765
PCT Pub. Date: Sep. 24, 2020

(65) Prior Publication Data
US 2022/0142612 A1 May 12, 2022

(30) Foreign Application Priority Data
Mar. 18, 2019 (EP) .................................... 19163426

(51) Int. Cl.
*A61B 8/00* (2006.01)
*A61B 8/08* (2006.01)
(Continued)

(52) U.S. Cl.
CPC .............. *A61B 8/463* (2013.01); *A61B 8/085* (2013.01); *A61B 8/4245* (2013.01); *A61B 8/469* (2013.01);
(Continued)

(58) Field of Classification Search
CPC ....... A61B 8/463; A61B 8/085; A61B 8/4245; A61B 8/469; A61B 8/5215; A61B 8/5207;
(Continued)

(56) References Cited

U.S. PATENT DOCUMENTS 5,623,928 A 4/1997 Wright et al.
5,924,991 A * 7/1999 Hossack ............. G01S 15/8993
600/443
(Continued)

FOREIGN PATENT DOCUMENTS

JP   H07328007 A   12/1995
JP   2011104137 A   6/2011
WO   2014080319 A1   5/2014

OTHER PUBLICATIONS

PCT/EP2020/056913 ISR & Written Opinion, May 18, 2020.
(Continued)

*Primary Examiner* — Alexei Bykhovski

(57) ABSTRACT

The invention provides for a method for switching between fields of view of an ultrasound probe. The method begins by obtaining an anatomical model representing a region of interest of a subject and establishing a first field of view relative to an ultrasonic probe, wherein the first field of view comprises an initial portion of the region of interest. Ultrasound data is then obtained from the first field of view by way of the ultrasonic probe and a first anatomical feature is identified within the first field of view based on the ultrasound data. A location in digital space of the first field of
(Continued)

view relative to the anatomical model is determined based on the first anatomical feature. A second field of view is then established based on the anatomical model and the first field of view, wherein the first field of view functions as a reference field of view. The field of view is then switched from the first field of view to the second field of view.

15 Claims, 4 Drawing Sheets

(51) Int. Cl.
G06T 7/11 (2017.01)
G06T 17/20 (2006.01)
(52) U.S. Cl.
CPC .............. *A61B 8/5215* (2013.01); *G06T 7/11* (2017.01); *G06T 17/20* (2013.01); *G06T 2207/10132* (2013.01); *G06T 2207/30044* (2013.01); *G06T 2207/30048* (2013.01)
(58) Field of Classification Search
CPC ........... A61B 8/5269; A61B 8/54; A61B 8/08; A61B 8/0883; A61B 8/465; G06T 7/11; G06T 17/20; G06T 2207/10132; G06T 2207/30044; G06T 2207/30048
See application file for complete search history.

(56) References Cited

U.S. PATENT DOCUMENTS

| | | |
|---|---|---|
| 5,997,479 A | 12/1999 | Savord et al. |
| 6,013,032 A | 1/2000 | Savord |
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 2008/0285824 A1 | 11/2008 | Wildes et al. |
| 2009/0054775 A1 | 2/2009 | Kato et al. |
| 2014/0187946 A1 | 7/2014 | Miller et al. |
| 2015/0193972 A1* | 7/2015 | Algreatly ................. G06T 3/60 345/420 |
| 2016/0249885 A1 | 9/2016 | Schneider et al. |
| 2016/0287214 A1 | 10/2016 | Ralovich et al. |
| 2017/0196540 A1 | 7/2017 | Dufour et al. |
| 2017/0245815 A1* | 8/2017 | Allaire ................... A61B 6/503 |
| 2017/0251988 A1 | 9/2017 | Weber et al. |
| 2017/0296148 A1* | 10/2017 | Niemiec ............. A61B 8/4444 |
| 2017/0337680 A1 | 11/2017 | Weber et al. |
| 2017/0360396 A1* | 12/2017 | Peters ....................... G06T 7/75 |
| 2018/0085096 A1* | 3/2018 | Brandl .................. A61B 8/469 |
| 2018/0092626 A1 | 4/2018 | Waechter-Stehle et al. |

OTHER PUBLICATIONS

Ecabert et al: "Automatic Model-Based Segmentation Ofthe Heart in CT Images"; IEEE Transactions on Medical Imaging, vol. 27, No. 9, Sep. 2008, pp. 1189-.

\* cited by examiner

METHODS AND SYSTEMS FOR ADJUSTING THE FIELD OF VIEW OF AN ULTRASOUND PROBE

CROSS-REFERENCE TO PRIOR APPLICATIONS

This application is the U.S. National Phase application under 35 U.S.C. § 371 of International Application No. PCT/EP2020/056913, filed on Mar. 13, 2020, which claims the benefit of European Patent Application No. 19163426.0, filed on Mar. 18, 2019. These applications are hereby incorporated by reference herein.

FIELD OF THE INVENTION

The invention relates to the field of ultrasound imaging, and more specifically to the field of ultrasound imaging methods employing multiple fields of view.

BACKGROUND OF THE INVENTION

Ultrasound has many advantages, but one limitation of typical ultrasound technologies is the relatively small field-of-view and the trade-off between field of view size and frame rate, particularly in 3D ultrasound imaging. Images with larger regions (such as the left heart) have limited spatial and temporal resolution, while other, zoomed images (such as the heart valves) have higher spatial and temporal resolution.

Therefore, it is common that during a procedure, a user acquires a set of multiple images each targeting a different anatomical region. Some of the acquired images may be standard views (such as a magnified view of a mitral valve). Other images may be very specific to the subject and topic of investigation (for example, focusing on a detected structural abnormality).

After the user has acquired multiple different fields of view (which may include non-standard views), they may want to switch back and forth between the various views, for example, for comparison or for checking the effect of a treatment in an interventional procedure. As long as the probe is stationary, this is possible by simply remembering the initial acquisition parameters of the various fields of view. Probe movements (intentionally or accidentally), however, would make these settings invalid.

Further, it may be that the user is required to quickly switch between different fields of view in the scanning region, for example, between a full volume image to assess heart wall motion and a zoomed image to assess detailed mitral leaflet dynamics. As discussed above, changing the field of view typically requires some manual readjustment of the scanning parameters, which makes very fast switching impossible.

Even if settings for different anatomical regions would be identified in the first place, subsequent probe movements would make these settings invalid. Identification using normal heart segmentation is typically too slow to provide a fast first estimate or to account for probe movements.

There is therefore a need for a means of switching between field of view of an ultrasound probe in a more robust and accurate manner.

Document US 2014/0187946 discloses a method for active control of ultrasound image acquisition including accessing image data representing a series of ultrasound images acquired over a period of time.

SUMMARY OF THE INVENTION

The invention is defined by the claims.

According to examples in accordance with an aspect of the invention, there is provided a method for switching between fields of view of an ultrasound probe, the method comprising:

obtaining an anatomical model representing a region of interest of a subject, wherein the anatomical model comprises anatomical information;

establishing a first field of view relative to an ultrasonic probe, wherein the first field of view comprises an initial portion of the region of interest;

obtaining ultrasound data from the first field of view by way of the ultrasonic probe;

identifying a first anatomical feature within the first field of view based on the ultrasound data;

determining a location in digital space of the first field of view relative to the anatomical model based on the first anatomical feature;

establishing a second field of view based on the anatomical model and the first field of view, wherein the second field of view is outside of the first field of view and the first field of view functions as a reference field of view, and wherein establishing the second field of view comprises extrapolating the location of the second field of view based on the first anatomical feature; and switching from the first field of view to the second field of view.

The method provides for automatic switching between fields of view of an ultrasound probe based on an anatomical model.

The anatomical model represents a region of interest, such as a heart or a fetus. A first field of view is then established comprising a portion of the region of interest.

In other words, the first field of view covers an area of the subject that corresponds to at least a portion of the area represented by the anatomical model.

An anatomical feature is identified within the first field of view based on obtained ultrasound data. The location of the first field of view is then determined in the same space as the anatomical model.

The location of the first field of view may be used in conjunction with the anatomical model to automatically determine, and switch to, one or more alternative fields of view.

In an embodiment, the method further comprises updating the location of the first field of view in digital space, wherein updating the location of the first field of view comprises:

obtaining first further ultrasound data from the first field of view;

determining an updated location of the first anatomical feature within the first field of view based on the first further ultrasound data; and determining an updated location in digital space of the first field of view relative to the anatomical model based on the updated location of the first anatomical feature.

In this way, the method provides for a means of checking the contents of the first field of view relative to the anatomical model. Thus, the location of the first field of view in digital space may be tracked over time. The most recent contents of the first field of view may then be used to establish the second field of view, thereby accounting for movements of the ultrasound probe, or movements within the region of interest (such as fetal movements).

The further ultrasound data may be obtained in a continuous manner, or at regular intervals (such as regular time intervals), depending on the application.

Further, this may allow for the reestablishing of the first field of view after a pause in the obtaining of the ultrasound data.

In an embodiment, the method further comprises adjusting the second field of view, wherein adjusting the second field of view comprises:

obtaining second further ultrasound data from the second field of view;

identifying a second anatomical feature within the second field of view based on the second further ultrasound data;

determining a location in digital space of the second field of view relative to the anatomical model based on the identified second anatomical feature; and adjusting the second field of view based on the determined location of the second field of view.

In this way, the second field of view may be adjusted to compensate for any residual error that may arise during the switching process.

In an embodiment, the anatomical model comprises a pre-encoded field of view and wherein establishing the second field of view comprises selecting the pre-encoded field of view.

In this way, additional fields of view may be automatically selected from a predetermined list within the anatomical model.

In an arrangement, establishing the second field of view comprises:

receiving a user input, wherein the user input indicates a desired field of view; and encoding the desired field of view as the second field of view into the anatomical model.

In this way, the user may define custom fields of view, which may then be encoded into the anatomical model.

In an embodiment, the identifying of the first anatomical feature comprises performing fast segmentation on the first ultrasound data.

In this way, the anatomical feature may be identified in near real time as the ultrasound data is being obtained.

In a further embodiment, performing the fast segmentation comprises adapting a triangular mesh to the first ultrasound data, wherein the triangular mesh comprises a plurality of triangles.

The triangular mesh may be used to identify an approximate location of an anatomical feature in order to facilitate the fast segmentation.

In an embodiment, the encoding the second field of view comprises flagging a triangle of the plurality of triangles as one of:

an interior triangle, wherein the interior triangle is within the second field of view and within a safety margin, wherein the safety margin defines an area within the second field of view;

a border triangle, wherein the border triangle is at least partially outside of the safety margin; and an exterior triangle, wherein the exterior triangle is outside of the second field of view.

In this way, the borders of the field of view may be defined based on the anatomical context within the triangles. Thus, the adjustment of the field of view may be based on the borders of the initial field of view as defined by the anatomy of the subject.

In an embodiment, the establishing of the field of view comprises one or more of:

establishing a primary angular extent along an azimuth direction;

establishing a secondary angular extent along an elevation direction;

establishing a scanning depth; and establishing an orientation of the ultrasonic probe.

In an arrangement, switching from the first field of view to the second field of view is performed automatically, or in response to a user input.

In an embodiment, the method comprises performing a single-shot multi-zoom acquisition on the first field of view and the second field of view.

In this way, the fields of view may be imaged across a short period of time, thereby reducing the time delay between the acquisition of each field of view. Thus, there is little delay due to the user manually adjusting the field of view, which may lead to an increase in the accuracy of the final images. In other words, the fields of view are acquired rapidly, one after another. For example, the single-shot multi-zoom may be performed across a single heartbeat.

According to examples in accordance with an aspect of the invention, there is provided a computer program comprising computer program code means which is adapted, when said computer program is run on a computer, to implement the methods described above.

According to examples in accordance with an aspect of the invention, there is provided a medical system adapted to adjusting a field of view of an ultrasound probe, the system comprising:

an ultrasound probe adapted to acquire ultrasound data; and a processor, wherein the processor is adapted to:
obtain an anatomical model representing a region of interest of a subject, wherein the anatomical model comprises anatomical information;
establish a first field of view relative to an ultrasonic probe, wherein the first field of view comprises an initial portion of the region of interest;
obtain ultrasound data from the first field of view by way of the ultrasonic probe;
identify a first anatomical feature within the first field of view based on the ultrasound data;
determine a location in digital space of the first field of view relative to the anatomical model based on the first anatomical feature;
establish a second field of view based on the anatomical model and the first field of view, wherein the second field of view is outside of the first field of view and the first field of view functions as a reference field of view, and wherein establishing the second field of view comprises extrapolating the location of the second field of view based on the first anatomical feature; and
switch from the first field of view to the second field of view.

In an embodiment, the system further comprises a display adapted to display the ultrasound data to a user in the form of an ultrasound image.

In an embodiment, the system further comprises a user interface adapted to receive a user input.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
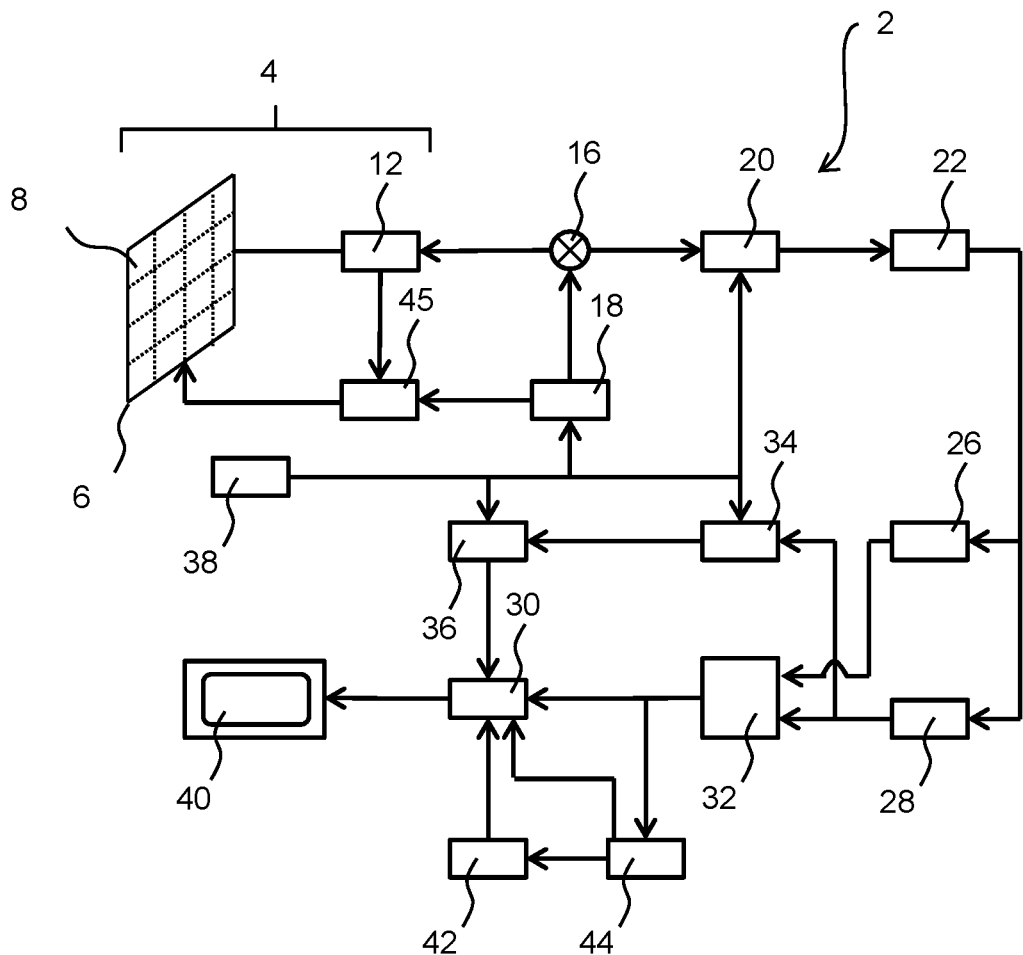
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides for a method for switching between fields of view of an ultrasound probe. The method begins by obtaining an anatomical model representing a region of interest of a subject and establishing a first field of view relative to an ultrasonic probe, wherein the first field of view comprises an initial portion of the region of interest. Ultrasound data is then obtained from the first field of view by way of the ultrasonic probe and a first anatomical feature is identified within the first field of view based on the ultrasound data.

A location in digital space of the first field of view relative to the anatomical model is determined based on the first anatomical feature. A second field of view is then established based on the anatomical model and the first field of view, wherein the first field of view functions as a reference field of view. The field of view is then switched from the first field of view to the second field of view.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The methods described herein may be performed on a processing unit. Such a processing unit may be located within an ultrasound system, such as the system described above with reference to FIG. 1. For example, the image processor 30 described above may perform some, or all, of the method steps detailed below. Alternatively, the processing unit may be located in any suitable system, such as a monitoring system, that is adapted to receive an input relating to a subject.

Figure 2:
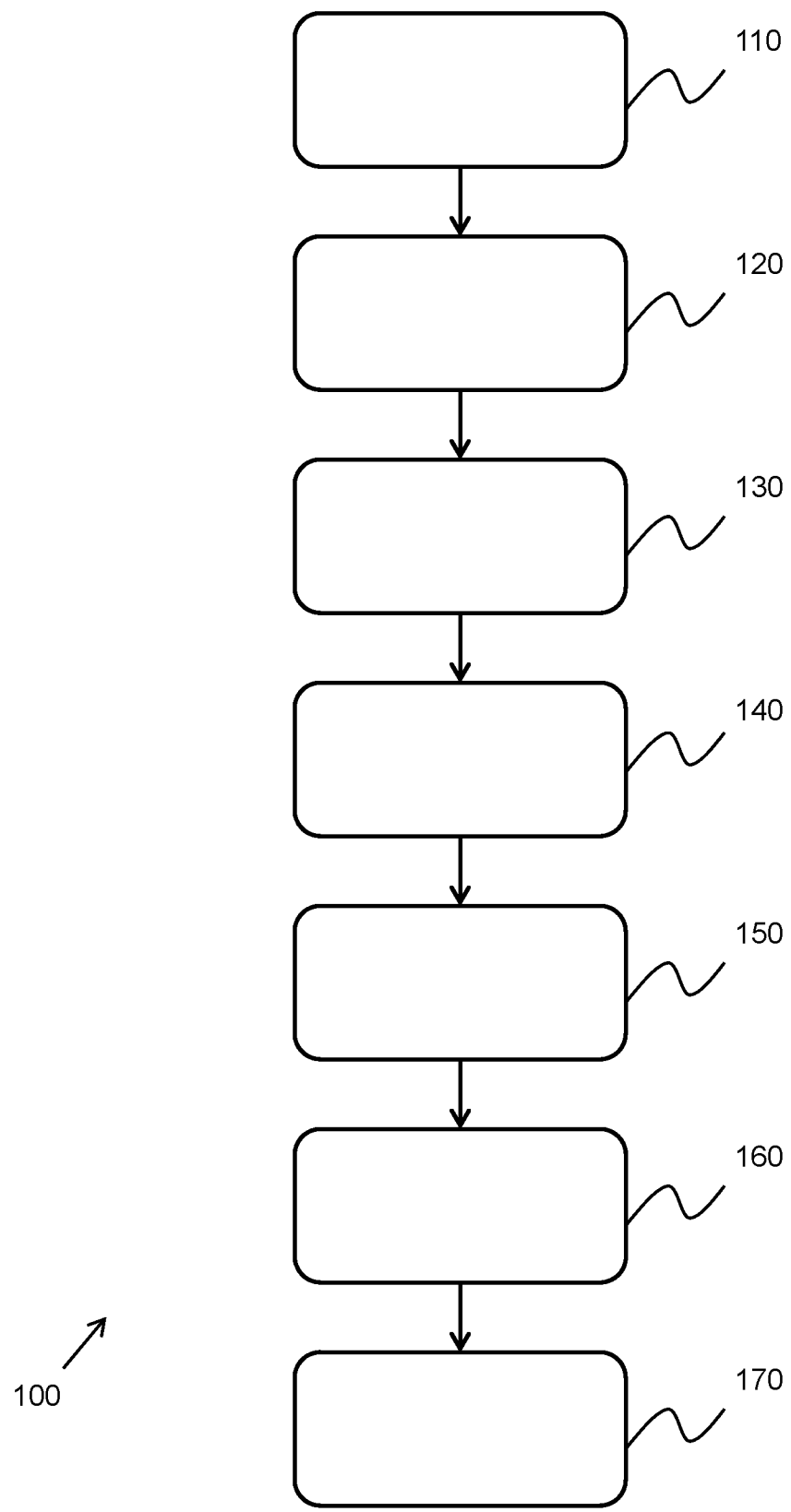
FIG. 2 shows a method of the invention.

FIG. 2 shows a method 100 for switching between fields of view of an ultrasound probe.

The method begins in step 110 by obtaining an anatomical model representing a region of interest of a subject.

The anatomical model may represent any part of the anatomy under investigation. For example, the anatomical model may represent all, or part, of the heart of the subject. The anatomical model may, for example, represent the left side of the heart or the mitral valve. Alternatively, the anatomical model may represent all, or part, of a fetus.

The anatomical model may be any type of model suitable for representing an anatomical region. For example, the anatomical model may be a mesh model or a set of anatomical landmarks with geometrical relations to each other.

In step 120, a first field of view is established relative to an ultrasonic probe. The field of view comprises an initial portion of a region of interest of a subject.

The establishing of the field of view may be performed in a number of steps. In order to establish a field of view for a 2D ultrasound image, the establishing of the field of view may include establishing a primary angular extent along an azimuth direction and establishing a scanning depth. If the field of view is to be extended to capture a 3D ultrasound image, the establishing of the field of view may further comprise establishing a secondary angular extent along an elevation direction. Further, the establishing of the field of view may include establishing an orientation of the ultrasonic probe relative to the subject.

In addition, the establishing of the field of view may include receiving a user input. For example, a user may select a region of interest within an ultrasound image, which may then be defined as the field of view. Alternatively, the user may select a standard clinical setting, which may then be used as a basis for establishing the field of view.

In step 130, ultrasound data is obtained from the first field of view by way of the ultrasonic probe. The ultrasound data may comprise B-mode ultrasound image data, which represents structural data, and/or color Doppler ultrasound data, which represents motion within the field of view.

In step 140, a first anatomical feature is identified within the field of view based on the initial ultrasound data.

The anatomical feature may be any feature associated with the anatomy of a subject. For example, the anatomical feature may comprise: bone; soft tissue; a part of an organ; a blood vessel; a fluid; and the like.

The identifying of the anatomical feature may comprise performing fast segmentation on the initial ultrasound data. In other words, the acquired ultrasound data may be roughly segmented in order to identify an approximate location of the anatomical feature within the field of view. In the example where the region of interest comprises the heart, the fast segmentation may be based on a fast heart model.

By way of example, the fast segmentation may include generating a triangular mesh based on the ultrasound data and encoding the plurality of triangles with anatomical information.

Put another way, the result of the segmentation is, for example, an adapted triangular mesh, in which anatomical information such as plane location is encoded in the triangles. The fast segmentation can be achieved by, for example: using more efficient boundary detectors, which may be adapted to determine image gradients from fewer points than standard models; using a minimal set of processing iterations; and/or using numerical methods which favor speed over high accuracy.

Each triangle of the triangular mesh contains some anatomical information, such as which triangle belongs to which region or view. Each triangle may be labelled according to the contained anatomical information. The triangular mesh may be deformed, or adapted, based on the anatomical feature(s) detected in the ultrasound data, such that each triangle may be placed at a location that fits the content of the ultrasound data. Using, for example, the labels of each triangle, which may be carried through the adaptation of the triangular mesh, may then add anatomical context to the obtained ultrasound data.

In an example, volumetric information may be encoded into the plurality of triangles as the anatomical information. In other words, all triangles of, for example, the mitral valve are labeled to encode the 3D volume occupied by it. The acquisition parameters of the ultrasonic probe may then be adjusted to acquire the 3D volume containing the mitral valve. Standard fields of view may be encoded in this way and may be further enriched with information on which 2D planes (plane information) cut through the 3D volume of interest.

In the example that the fast segmentation described above results in a triangular mesh, the encoding of the field of view may include flagging a triangle of the plurality of triangles as one of: an interior triangle, wherein the interior triangle is within the field of view and within a safety margin, wherein the safety margin defines an area within the field of view; a border triangle, wherein the border triangle is at least partially outside of the safety margin; and an exterior triangle, wherein the exterior triangle is outside of the field of view. It should be noted that the indices of the triangles may be used, rather than the full triangle.

In other words, it is possible to encode a field of view based on anatomical context. The encoding may then be used to remember the triangles that intersect with the boundary of the field of view when acquiring the initial ultrasound data (particularly if the object of interest is larger than the actual field of view). Alternatively, the encoding may be used to remember which triangles are inside/outside the field of view from a set of anatomically relevant landmarks.

In step 150, the location, in digital space, of the first field of view is determined relative to the anatomical model based on the first anatomical feature.

As the anatomical model is a digital representation of a part of the anatomy of a subject, it can be understood that the anatomical model occupies digital space as opposed to real space. The first field of view encompasses an area of the anatomy of the subject, which occupies real space. Thus, an anatomical feature may be used to register the location of the first field of view in the digital space occupied by the anatomical model.

In step 160, a second field of view is established based on the anatomical model and the first field of view. In this case, the first field of view functions as a reference field of view for the establishment of the second field of view. The second field of view may be established by extrapolating its location with respect to the first field of view based on the anatomical feature within the first field of view.

Put another way, when the first field of view, or current field of view, has been registered against the anatomical model, it is possible to determine one or more additional target fields of view.

For example, the first field of view may contain the left side of a heart of a subject. The location of the first field of view relative to the anatomical model in digital space may be determined by comparing the location of the left atrium and/or left ventricle, which may act as the anatomical feature(s) in the first field of view, to those in the anatomical model of the heart.

Following this determination, a second field of view, or target field of view, may be established based on the first field of view and the anatomical model. For example, in the case where the first field of view comprises the left side of the heart, the second field of view may be established to include the right side of the heart.

The anatomical model may comprise one or more pre-encoded fields of view. In this case, establishing the second field of view may include selecting a pre-encoded field of view based on the first field of view.

Returning to the example above, the anatomical model of the heart may include pre-encoded fields of view of both the left side of the heart and the right side of the heart. When the user positions the ultrasonic to commence the examination, they may be presented with a list of fields of view, which they may select from to obtain ultrasound data from said field of view. The list of fields of view may be a list of fields of view that are available from the current position of the probe. For example, the ultrasonic probe may perform a scouting scan, which may then be used to determine one or more available fields of view to be presented to the user. The user may switch between the pre-encoded fields of view presented to them, or establish a custom field of view, which may then be encoded into the anatomical model.

Alternatively, or in addition, to the pre-encoded field of view, the user may define a desired field of view. In this case, establishing the second, or target, field of view may comprise receiving a user input, wherein the user input indicates a desired field of view, establishing the desired field of view as the second field of view and encoding the second field of view into the anatomical model.

In other words, the user may manually set any field of view, which may then be returned to at a later stage in order to review the same or (if not possible from a new probe position) a similar area.

As the anatomy contained within the target field of view may be outside the current field of view, the location of the target field of view may be extrapolated from the anatomical feature within the current field of view. For example, if the first field of view contains a view of the mitral valve, the anatomical model may establish anatomical context and the position of the aortic valve, for example, may be extrapolated, and the field of view switched to show the aortic valve.

In step 170, the field of view of the ultrasonic probe is switched from the first field of view to the second field of view.

In this way, the ultrasonic probe may automatically switch between fields of view based on a single acquisition by a user. In this way, the user need not move or adjust the probe in order to capture a number of fields of view.

It should be noted that the method described above is not limited to two fields of view but may be used to switch from the first field of view to any number of alternative fields of view.

This is illustrated in the following example. In a first step, an image of the first field of view is acquired, for example showing the full left ventricle. Based on the anatomical context within the image, the ultrasound probe may switch to a second field of view, for example a pre-encoded mitral valve zoom image. Following these acquisitions, and based on the updated anatomical context taken from the first field of view and the second field of view, the ultrasound probe may switch to a third field of view. The third field of view may be another pre-encoded view, such as an aortic valve zoom image. It should be noted that it is not necessary for the probe to return to the first field of view before switching to the third field of view.

The user may then manually define a fourth, non-standard view; which is then encoded into the anatomical model and remembered. Based on the anatomical context within any of the imaged fields of view, the probe may then switch back to second field of view (showing, for example, the mitral valve). The user may continue to switch between fields of view until the investigation is completed. Any of the fields of view captured by the ultrasonic probe may be used as a reference field of view for establishing a target field of view based on the imaged anatomical context. In some embodiments, the first field of view is used as a reference for some, or even all, of the other fields of view. In other embodiments, a current field of view is used as a reference for a next field of view, i.e., the field of view the user wants to switch to. In such embodiments, the notion of "first" and "second" field of view is to be regarded in relative terms rather than in absolute terms. In yet some other embodiments, a given field of view is used as a reference for a first subset of fields of view, while another field of view is used as a reference for a second subset of fields of view. Each of the first and second subsets of fields of view may comprise one or more fields of view, and the field(s) of view of the first subset is/are different from the field(s) of view of the second subset.

The method may further include updating the location of the first field of view in digital space.

The location of the first field of view may be updated by obtaining first further ultrasound data from the first field of view and determining an updated location of the first anatomical feature within the first field of view based on the first further ultrasound data. An updated location of the first field of view relative to the anatomical model may then be determined based on the updated location of the first anatomical feature.

In other words, the position of the first field of view relative to the anatomical model in digital space may be refined by obtaining further ultrasound data from the first field of view. The further ultrasound data may be obtained in a continuous manner, thereby allowing for continuous updating of the location of the first field of view, or at discrete time intervals.

In this way, the establishment of the second field of view may be performed on the most up to date anatomical context contained within the first field of view, thereby increasing the accuracy of the switch from the first field of view to the second field of view.

The method may further comprise adjusting an acquisition setting of the ultrasound probe based on the updated location of the first field of view.

The method may also comprise the step of adjusting the second field of view. Adjusting the second field of view may include obtaining second further ultrasound data from the second field of view and identifying a second anatomical feature within the second field of view based on the second further ultrasound data.

A location of the second field of view relative to the anatomical model in digital space is determined based on the identified second anatomical feature and the second field of view is adjusted based on the determined location of the second field of view.

In other words, after switching from the first field of view to the second field of view based on the anatomical model, there may be some error or misalignment. The second anatomical feature, detected in the ultrasound data acquired from the second field of view, may be used to adjust the second field of view. In this way, the accuracy of the second field of view may be increase.

During, or after the examination, the ultrasonic probe may be removed from the surface of the subject's skin and repositioned. The user may then attempt to return the ultrasonic probe to the initial imaging position in order to obtain further ultrasound data from the first field of view, or any other field of view imaged prior to the movement of the probe.

In this case, it may be determined whether the field of view in question has moved relative to the initial portion of the region of interest between obtaining the initial ultrasound data and obtaining the further ultrasound data based on the identified anatomical feature.

For example, determining whether the field of view has moved may include re-establishing the location of the anatomical feature identified in the initial ultrasound data. This may include identifying an initial location of the triangle relative to the anatomical feature based on the initial ultrasound data and identifying a further location of the triangle relative to the anatomical feature based on the further ultrasound data. The initial location and the further location are then compared and it is determined whether the field of view has moved relative to the initial portion of the region of interest based on the comparison. The field of view may then be updated based on the determination.

In other words, from the current probe position and the identified anatomical feature (which may be up-to-date according to the current probe position due to the fast segmentation tracking), it is possible to determine the required ultrasound acquisition parameters to reproduce the encoded field of view as closely as possible.

As discussed above, the main ultrasound acquisition parameters for a 3D probe are: angular extent along the primary acquisition direction (azimuth); angular extent along the secondary acquisition direction (elevation); radial dimension (minimal scanning depth, maximal scanning depth); and transducer rotation (scan/omniplane angle).

For the case in which the original anatomy still lies completely within the maximum scanning region of the probe, the new parameters may be derived as follows. For the angular and radial extent parameters, an upper and lower boundary is calculated to contain the encoded anatomy and potentially add some safety margin to the boundaries.

For the case in which part of the original anatomy lies outside the maximum scanning region of the probe, the following procedure may be followed.

For the angular and radial extent parameters, upper and lower boundaries are calculated to contain the encoded anatomy. Where the desired boundaries lie outside the maximum scanning region of the ultrasound probe, restrict the boundary to the maximum scanning region. If transducer rotation is available, attempt to use a different rotation setting that allows the field of view cover a larger region of the desired anatomy.

The acquisition parameters may be adjusted according to a hierarchy, for example because the probe position does not allow for the capture of the desired anatomy without other drawbacks (such as, the field of view becoming too large to achieve a desired frame rate). In this case, further heuristics can be used to decide how to define the field of view boundaries. Examples include: giving a higher priority to those regions also present in other fields of view, because they are deemed more important to the examination; giving a lower priority to those regions also present in other fields of view, because they can be inspected in those fields of view; or using prior knowledge encoded in the model to decided which regions are typically more or less important.

Alternatively, rather than adjusting the acquisition parameters of ultrasonic probe, the remembered contents of the field of view in question may simply be updated to contain the current anatomical features based on the newly acquired ultrasound data. Any alternative fields of view that were established based on the newly updated field of view may also be updated to accommodate this new information.

For example, a first field of view contains a left atrium and a second field of view is established to image a right atrium. During the ultrasound examination, the ultrasonic probe may move such that the acquisition parameters of the first field of view, that were previously used to image the left atrium, now result in a view of the left ventricle. The system may update the anatomical feature within the first field of view, thereby updating the first field of view based on the new anatomical context. The system may also update the parameters used to switch between the first and second fields of view, so that the second field of view will maintain a view of the right atrium, despite the shift in probe location.

Figure 3:
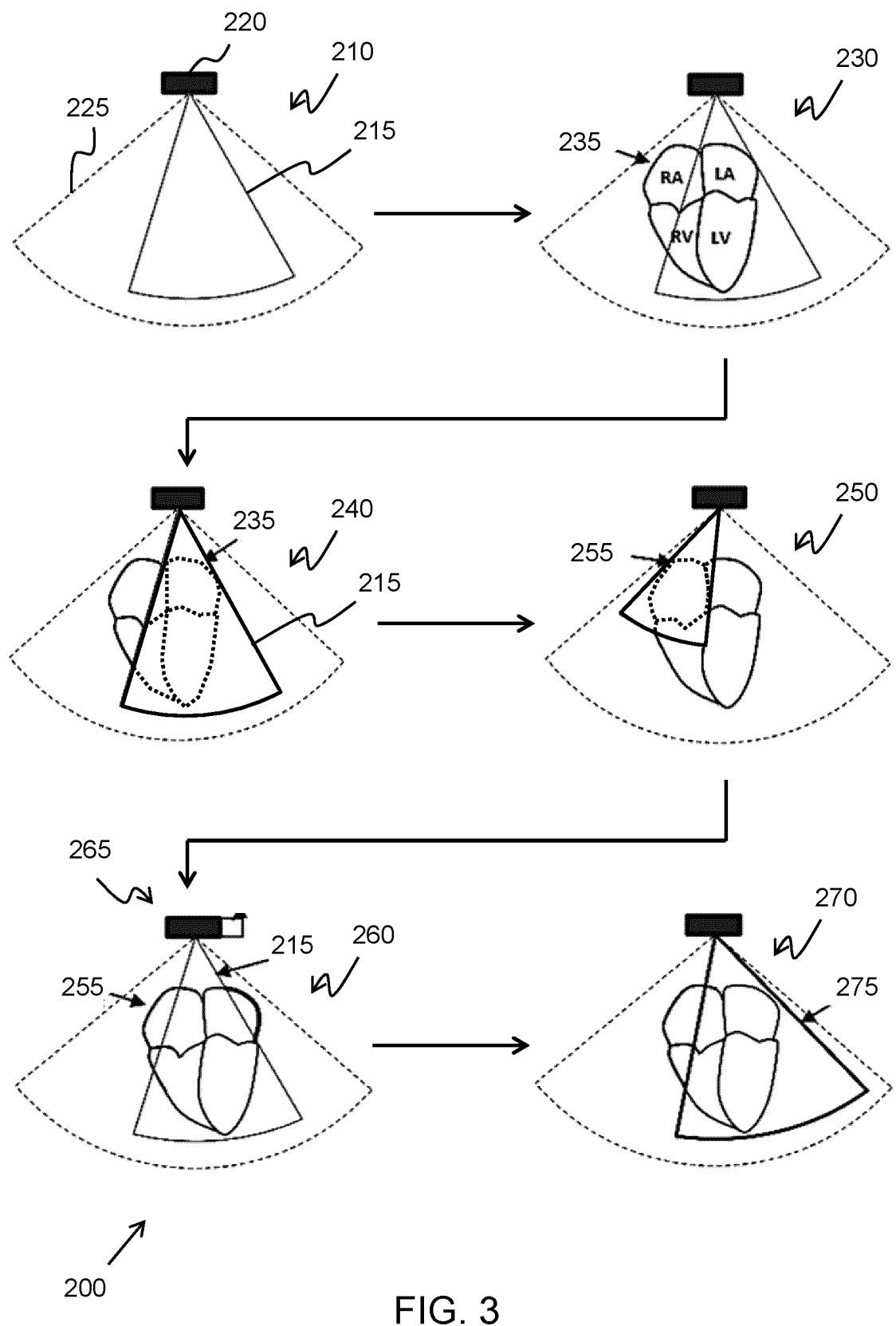
FIG. 3 shows a graphical representation of a method of the invention.

FIG. 3 shows a graphical representation 200 of the methods described above using fields of view defined by the user.

In the first stage 210, a first field of view 215 is established relative to the ultrasound probe 220. The ultrasound probe has a maximum scanning region 225 given by physical and engineering constraints. Typically, a field of view 215 within these constraints is selected as the current scanning region.

In the second stage 230, a fast segmentation model may be used to identify an anatomical feature and provide anatomical context within the field of view. In this example, the anatomical features include the heart chambers, where: LA represents the left atrium; LV represents the left ventricle; RA represents the right atrium; and RV represents the right ventricle.

In the third stage 240, the field of view, which in this case is a user-defined field of view, is encoded into the model based on the anatomical features 235. In this example, all of the model triangles inside the field of view, represented by the dashed lines within the first field of view 215, are stored.

In stage 250, after readjusting the scan parameters, a user-defined second field of view 255 is established based on the first field of view and the anatomical model and switched to. Again, all model triangles inside the second field of view, represented by the dashed lines within the second field of view, are remembered.

At a later point during the examination, shown in stage 260, the user wants to acquire an image of the first field of view region again. However, the probe position 265 has changed in the meantime. If the anatomical context was to be neglected and only the original scan settings were restored, a part of the originally shown anatomy would be outside the field of view 215 (contour shown in bold).

However, if the scanning parameters are re-calculated based on the tracked anatomical context as shown in stage 270, the complete original anatomical region can be automatically acquired again by way of the adjusted field of view 275.

In summary, the principle of the method is to first generate anatomical context in the image (for example, using model-based segmentation), which may then be used to switch to alternative fields of view relative to the anatomy (such as, by remembering which parts of the anatomy were inside/outside of the field of view, or which anatomical landmarks marked the border of the field of view). The fields of view may be standard fields of view, which are pre-encoded into the anatomical model, or user-defined fields of view. Then, the anatomical feature may be tracked using the current field of view and a fast segmentation model.

Based on the tracking and the updated anatomical context, the fields of view established at the initial probe positions may be transferred to the new probe position. While the tracking is performed in the current field of view only, the regions comprised in other user-defined fields of view may be extrapolated. This tracking in near real-time provides for a means of switching between the fields of view, even from the new probe position.

If possible, the entire content of the original field of view may be fully displayed from the new probe position. If this is not possible (for example, because some part has moved outside the maximum scanning region of the probe), a field of view may be calculated that resembles the original field of view as closely as possible. In this way, the system remembers the preferred anatomical fields of view even when the probe is moved.

In order to perform the method in near real time, a fast automatic identification of the anatomical feature within the field of view is used, for example, using a very fast heart model. The fast segmentation may be achieved by using more efficient boundary detectors or fewer model iterations as described above. From the adapted model, the locations of relevant anatomical field of view regions are defined. This allows the user to rapidly switch between typical standard views, or user-defined views, even after probe movement. In particular, the fast segmentation model is required to generate frequent updates of the anatomical information in case the probe is being moved.

Figure 4:
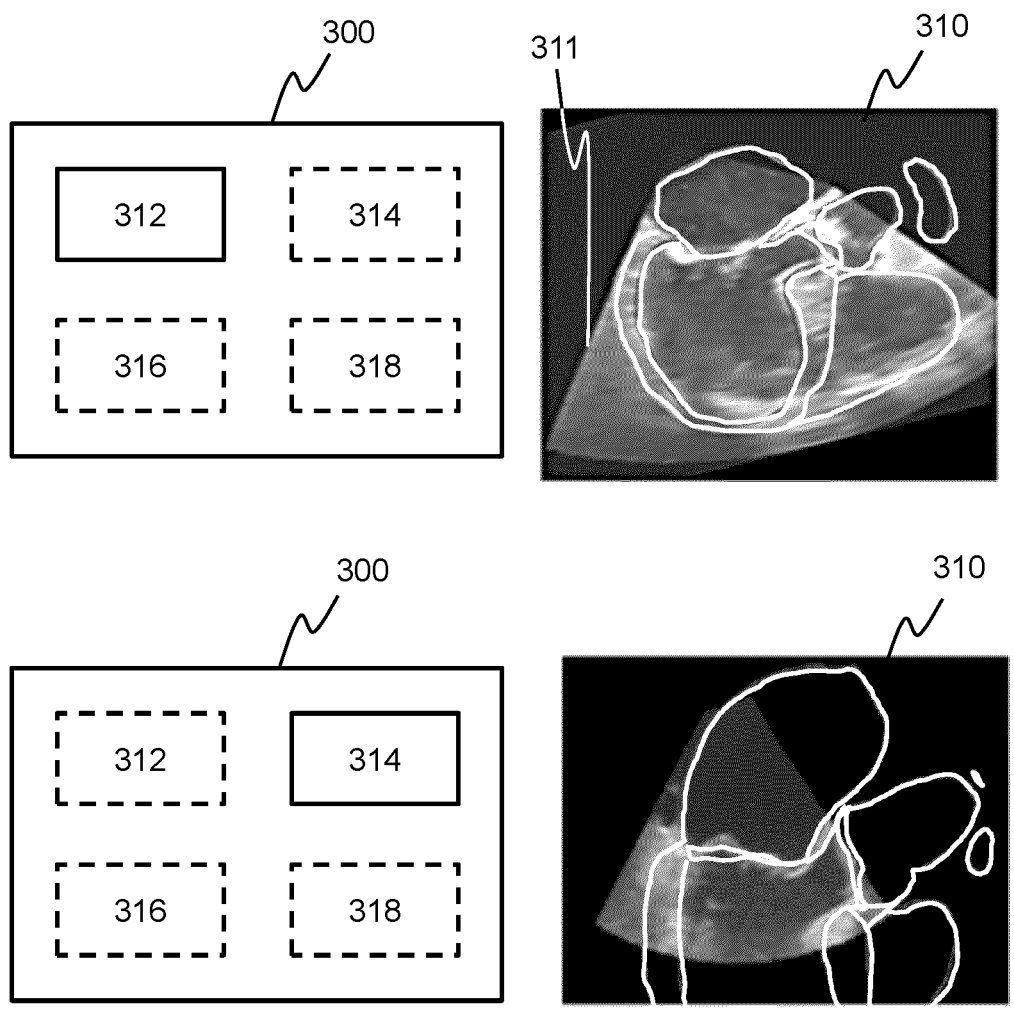
FIG. 4 shows a schematic representation of a user interface and associated display.

FIG. 4 shows an example of a user interface 300 and a display 310 for displaying an ultrasound image. The display is adapted to show a field of view 311 associated with a given graphical element 312.

The user interface 300 may provide a selection list 312, 314, 316, 318 of available fields of view on an interface of an ultrasound system. The user may then freely select any desired field of view during ultrasound data acquisition. Probe movements may be compensated by updating the acquisition parameters in near real-time based on the anatomical information as described above.

In other words, a user interface 300 may present all available field of view options to a user, and the user may select the desired one. Fast switching between the fields of view may be possible even after probe movement, as anatomical information is frequently updated by the fast model as describe above.

The fields of view may be acquired by way of single-shot multi-zoom acquisitions. These acquisitions entail capturing a set of defined field of view within a few heart beats and without further user interaction. For example, during the first beat an image showing full left heart may be captured, an anatomical feature identified, and on consecutive beats mitral valve and aortic valve zoom images are captured.

In this way, there is no delay due to the user manually adjusting the field of view. The resulting short time span between the different capture points may improve the physiological comparability of the displayed anatomies. Therefore, the images may be more comparable than if some length of time elapses between their capture.

In this case, the method described above may identify the respective subregions from an initial scan, and immediately after that, a series of zoom images are acquired during one heartbeat. For example, a mitral valve image may be acquired while the mitral valve is closed, and an aortic valve image may be acquired while the aortic valve is closed. Then, based on the identified anatomy and information on heart phase, within one single heart beat, several zoom images may be acquired.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for switching between fields of view of an ultrasound probe, the method comprising:
    obtaining an anatomical model representing a region of interest of a subject, wherein the anatomical model comprises anatomical information;
    establishing a first field of view relative to an ultrasonic probe, wherein the first field of view comprises an initial portion of the region of interest;
    obtaining ultrasound data from the first field of view by way of the ultrasonic probe;
    identifying a first anatomical feature within the first field of view based on the ultrasound data;
    determining a location in digital space of the first field of view relative to the anatomical model based on the first anatomical feature;
    establishing a second field of view based on the anatomical model and the first field of view, wherein the first field of view functions as a reference field of view, and wherein establishing the second field of view comprises extrapolating a location of the second field of view with respect to the first field of view based on the first anatomical feature, wherein establishing the second field of view further comprises receiving a user input, wherein the user input indicates a desired field of view that is not a pre-encoded field of view, and encoding the desired field of view as the second field of view into the anatomical model, wherein encoding the second field of view comprises flagging a triangle of a plurality of triangles as one of:
    an interior triangle, wherein the interior triangle is within the second field of view and within a safety margin, wherein the safety margin defines an area within the second field of view;
    a border triangle, wherein the border triangle is at least partially outside of the safety margin; and
    an exterior triangle, wherein the exterior triangle is outside of the second field of view; and
    switching from the first field of view to the second field of view.

2. The method as claimed in claim 1, wherein the method further comprises updating the location in digital space of the first field of view, wherein updating the location of the first field of view comprises:
    obtaining first further ultrasound data from the first field of view;
    determining an updated location of the first anatomical feature within the first field of view based on the first further ultrasound data; and
    determining an updated location in digital space of the first field of view relative to the anatomical model based on the updated location of the first anatomical feature.

3. The method as claimed in claim 1, wherein the method further comprises adjusting the second field of view, wherein adjusting the second field of view comprises:
    obtaining second further ultrasound data from the second field of view;
    identifying a second anatomical feature within the second field of view based on the second further ultrasound data;
    determining a location in digital space of the second field of view relative to the anatomical model based on the identified second anatomical feature; and
    adjusting the second field of view based on the determined location of the second field of view.

4. The method as claimed in claim 1, wherein the anatomical model comprises a pre-encoded field of view and wherein establishing the second field of view comprises selecting the pre-encoded field of view.

5. The method as claimed in claim 1, wherein identifying the first anatomical feature comprises performing fast segmentation on the first ultrasound data.

6. The method as claimed in claim 5, wherein performing the fast segmentation comprises adapting a triangular mesh to the first ultrasound data, wherein the triangular mesh comprises a plurality of triangles.

7. The method as claimed in claim 1, wherein establishing the first field of view comprises one or more of:
    establishing a primary angular extent along an azimuth direction;
    establishing a secondary angular extent along an elevation direction;
    establishing a scanning depth; and
    establishing an orientation of the ultrasonic probe.

8. The method as claimed in claim 1, wherein switching from the first field of view to the second field of view is performed automatically, or in response to a second user input.

9. The method as claimed in claim 1, wherein the method comprises performing a single-shot multi-zoom acquisition on the first field of view and the second field of view.

10. A computer program comprising computer program code stored on non-transitory computer-readable medium which is adapted, when said computer program is run on a computer, to implement the method of claim 1.

11. The method of claim 1, wherein the second field of view is outside of the first field of view.

12. A medical system adapted to adjusting a field of view of an ultrasound probe, the system comprising:
   an ultrasound probe adapted to acquire ultrasound data; and
   a processor, wherein the processor is adapted to:
      obtain an anatomical model representing a region of interest of a subject, wherein the anatomical model comprises anatomical information;
      establish a first field of view relative to the ultrasound probe, wherein the first field of view comprises an initial portion of the region of interest;
      obtain ultrasound data from the first field of view by way of the ultrasound probe;
      identify a first anatomical feature within the first field of view based on the ultrasound data;
      determine a location in digital space of the first field of view relative to the anatomical model based on the first anatomical feature;
      establish a second field of view based on the anatomical model and the first field of view, wherein the first field of view functions as a reference field of view, and wherein establishing the second field of view comprises extrapolating a location of the second field of view with respect to the first field of view based on the first anatomical feature, wherein establishing the second field of view further comprises receiving a user input, wherein the user input indicates a desired field of view that is not a pre-encoded field of view, and encoding the desired field of view as the second field of view into the anatomical model, wherein encoding the second field of view comprises flagging a triangle of a plurality of triangles as one of:
      an interior triangle, wherein the interior triangle is within the second field of view and within a safety margin, wherein the safety margin defines an area within the second field of view;
      a border triangle, wherein the border triangle is at least partially outside of the safety margin; and
      an exterior triangle, wherein the exterior triangle is outside of the second field of view; and
         switch from the first field of view to the second field of view.

13. The system as claimed in claim 12, wherein the system further comprises a display adapted to display the ultrasound data to a user in the form of an ultrasound image.

14. The system as claimed in claim 12, wherein the system further comprises a user interface adapted to receive the user input.

15. The system of claim 12, wherein the second field of view is outside of the first field of view.

* * * * *